US00PP31375P2

(12) United States Plant Patent
Lim

(10) Patent No.: US PP31,375 P2
(45) Date of Patent: Jan. 21, 2020

(54) HYBRID TEA ROSE PLANT NAMED 'LIMKING'

(50) Latin Name: *Rosa hybrida*
Varietal Denomination: LIMking

(71) Applicant: Altman Specialty Plants, Inc, Vista, CA (US)

(72) Inventor: Peter Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,577

(22) Filed: Dec. 3, 2018

(51) Int. Cl.
*A01H 5/02* (2018.01)
*A01H 6/74* (2018.01)

(52) U.S. Cl.
USPC ..... Plt./134

(58) Field of Classification Search
USPC ..... Plt./101, 130, 134
See application file for complete search history.

(56) References Cited

PUBLICATIONS

Biltmore International Rose Trials—https://hedgerowrose.com/rose-gardening/2017/09/25/biltmore-international-rose-trials-2015-results/. Retrieved from the Internet on Aug. 19, 2019. (8 pages total).*

* cited by examiner

*Primary Examiner* — Susan McCormick Ewoldt
(74) *Attorney, Agent, or Firm* — Cassandra Bright

(57) ABSTRACT

A new and distinct hybrid tea *Rosa* cultivar named 'LIMking' is disclosed, characterized by large soft yellow flowers with a strong, sweet fragrance. Flowers are around 10 cm in diameter and drop petals cleaning after bloom is finished. Plants are upright, and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'LIMking'.

BACKGROUND OF THE INVENTION

The new *Rosa* cultivar is a product of a planned breeding program conducted by the inventor, Peter Lim. The objective of the breeding program was to produce vigorous new garden hybrid tea rose varieties for ornamental commercial applications. The cross resulting in this new variety was made during May of 2009.

The seed parent is the variety *Rosa* 'BAIlord', U.S. Plant Pat. No. 19,046. The pollen parent is the variety *Rosa* 'The Finest', unpatented. The new variety was selected in 2010 by the inventor in a group of seedlings resulting from the 2009 crossing, in a nursery in McMinville, Oreg.

Asexual reproduction of the new cultivar was performed by vegetative cuttings. This was first performed at a research greenhouse in in McMinville, Oreg. in June 2010 and has shown that the unique features of this cultivar are stable and reproduced true to type in successive generations.

SUMMARY OF THE INVENTION

The cultivar 'LIMking' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMking'

These characteristics in combination distinguish 'LIMking' as a new and distinct *Rosa* cultivar:

1. Vigorous hybrid tea rose plant
2. Large yellow flowers to about 10 cm in diameter
3. Strong resistance to black spot disease.
4. Petals drop off cleaning after bloom is finished.
5. Sweet fragrance Plants of the new cultivar 'LIMking' are similar to plants of the seed parent, in most horticultural characteristics, however, plants of the new cultivar 'LIMking' differ in the following:

1. The new variety is a tea rose, the seed parent is a shrub rose.
2. The new variety has larger and fewer petals than the seed parent.

Plants of the new cultivar 'LIMking' are similar to plants of the pollen parent in most horticultural characteristics, however, plants of the new cultivar 'LIMking' differs in the following;

1. The new variety has a yellow flower, the pollen parent has a white flower.

COMMERCIAL COMPARISON

Plants of the new cultivar 'LIMking' can be compared to the commercial variety *Rosa* 'Jactou', U.S. Plant Pat. No. 8,706. These varieties are similar in most horticultural characteristics, however 'LIMking' differs in the following:

1. 'LIMking' has a sweet fragrance, 'Jactou' has a musky fragrance.
2. 'Jactou' has darker yellow petals.

3. The new variety has an earlier blooming flower cycle than 'Jactou'.
4. The new variety is less susceptible to black spot and mildew than 'Jactou'.
5. The new variety is shorter than 'Jactou'.

Plants of the new cultivar 'LIMking' can also be compared to the variety *Rosa* 'Summer Love', unpatented. These varieties are similar in most horticultural characteristics, however 'LIMking' differs in the following:

1. 'LIMking' has a sweet fragrance, 'Summer Love' has no fragrance.
3. When the flowers are fully open, 'Summer Love' has a larger flower diameter.
4. Foliage of 'Summer Love' is a different shade of green.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'LIMking' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'LIMking'.

Market classification: Hybrid tea rose.

PROPAGATION

Time to initiate roots: About 15 days at approximately 20° C.

Time to produce a rooted cutting: About 35 days at approximately 20° C.

PLANT

Age of plant described: Approximately 2 years.

Growth habit: Upright.

Container size: 2 gallon.

Height: 80 cm.

Plant spread: 60 cm.

Rootstock: Own root.

Growth rate: Moderate.

Branching characteristics: Sympodial branching.

Length of primary lateral branches: Average range 20 to 30 cm.

Diameter of lateral branches: Approximately 5 to 7 mm.

Quantity branches: 3 to 6 main branches, weak lateral branching, average 2 lateral branches per main branch.

Branches: Young Wood.

*Diameter*.—Approximately 4 mm.

*Texture*.—Glabrous, scant quantity of thorns.

*Approximately density/quantity of thorns*.—Approximately 1 per linear cm.

*Color*.—Near Green 138A, no anthocyanin at nodes.

Branches: Old Wood.

*Diameter*.—Approximately 2.0 cm.

*Color*.—Near Grey-Brown 199D.

*Texture*.—Rough thick woody striations.

Thorns:

*Approximately density/quantity of thorns*.—Approximately 1 per linear cm. Sharp and hard.

*Color of thorns*.—Immature: Greyed-Orange 175A. Mature: Near Greyed-Orange 165D.

*Shape*.—Deltoid, moderately hooked.

*Height*.—Average 7 mm.

*Diameter*.—Base near 5 mm. Tip near 2 mm.

FOLIAGE

Leaf:

*Arrangement*.—Alternate and compound.

*Quantity*.—Average 9 to 12 per main branch.

*Internode*.—Average range 3.5 to 4.4 cm.

*Average length*.—Approximately 11.5 cm.

*Average width*.—Approximately 7.0 cm.

Rachis:

*Average length*.—Approximately 4.5 cm.

*Average diameter*.—Approximately 0.2 cm.

*Color*.—Near RHS Green 138A.

*Texture*.—Glabrous all surfaces.

Leaflet:

*Quantity*.—3 or 5 per leaf, most commonly 5.

*Average length*.—Approximately 4.5 cm.

*Average width*.—Approximately 3.3 cm.

*Shape of blade*.—Ovate.

*Apex*.—Acute.

*Base*.—Rounded.

*Margin*.—Serrate.

*Appearance of top surface*.—Slightly glossy.

*Appearance of bottom surface*.—Matte.

*Texture of top surface*.—Glabrous.

*Texture of bottom surface*.—Glabrous.

*Color*.—Young foliage upper side: Near Yellow-Green 144A. Young foliage under side: Near Yellow-Green 144B. Mature foliage upper side: Near Green 137A. Mature foliage under side: Near Green 138B.

*Venation*.—Type: Reticulate. Venation color upper side: Near Yellow-Green 144B. Venation color under side: Near Yellow-Green 144C.

Petiole:

*Average length*.—Approximately 3.0 cm.

*Average diameter*.—Approximately 0.2 cm.

*Color*.—Near Yellow-Green 144B.

*Texture*.—Glabrous.

FLOWER

Natural flowering season: Spring until Autumn.

Flower type and habit: Single terminal flower, tea rose type.

Rate of flower opening: Approximately 7 days from bud to fully opened flower.

Flower longevity on plant: 7 to 10 days, after fully opened.

Quantity of flowers: 9 to 12 per plant.

Flower size:

*Diameter*.—Approximately 10 cm.

*Height*.—Approximately 5.5 cm.

Peduncle:
*Length.*—5 to 6 cm.
*Diameter.*—0.4 cm.
*Color.*—Near RHS Green 138A.
Petals:
*Petal arrangement.*—Whorled, traditional tea rose type.
*Petal quantity.*—20 to 30.
*Length.*—4.5 cm.
*Width.*—4.0 cm.
*Shape.*—Broad delate to cordate.
*Margin.*—Entire, slightly curved down.
*Apex.*—Rounded to very shallowly lobed.
*Base.*—Broad attenuate.
*Texture.*—Glabrous all surfaces.
Color: Petals.
*When opening.*—Upper surface: Near RHS Yellow 4A. Lower surface: Near RHS Yellow 4A.
*Fully opened.*—Upper surface: Near RHS Yellow 4C, base 4B. Lower surface: Near RHS Yellow 4C, base 4B. Color Changes when aging, both surfaces: Near RHS Yellow 4D, base 4C.
Bud:
*Shape.*—Round.
*Length.*—Approximately 2.4 cm.
*Diameter.*—Approximately 1.8 cm.
*Color.*—Near Yellow 5B.
Sepals:
*Quantity.*—5.
*Length.*—4.5 to 6.5 cm.
*Width.*—0.9 cm.
*Shape.*—Narrow deltoid.
*Apex.*—Acuminate.
*Margin.*—Serrate.
*Color.*—Interior Surface: Near Green RHS 138A. Exterior Surface: Near Green RHS 138B.
*Texture.*—Densely pubescent upper and lower surfaces.
Receptacle:
*Length.*—1.1 cm.
*Width.*—0.7 cm.
*Shape.*—Conical.
*Color.*—Near RHS Green 143C.
Fragrance: Very strong, sweet fragrance.

REPRODUCTIVE ORGANS

Stamens:
*Quantity.*—Average range 50 to 70.
*Filament length.*—Approximately 0.7 to 1.1 cm.
*Filament color.*—Near Yellow 4D.
Anthers:
*Length.*—0.2 cm.
*Shape.*—Linear.
*Color.*—Near Yellow-Orange 20D.
*Pollen.*—Color: Greyed-Orange N170D. Quantity: Scant.
Pistil:
*Number.*—Approximately 30.
*Pistil length.*—Approximately 1.2 cm.
*Style.*—Length: Approximately 0.4 cm. Color: Near Green-Yellow 1D.
Stigma:
*Shape.*—Linear.
*Color.*—Near Yellow 10C.
*Ovary color.*—Near RHS White 155C.
*Ovary shape.*—Oblong.
*Ovary length.*—Average 0.5 cm.
*Ovary diameter.*—Average 0.2 cm.

OTHER CHARACTERISTICS

Seeds and fruits: Not observed.
Disease/pest resistance: Good overall disease resistance to normal pests and diseases typical of garden roses. Very good resistance to blackspot diseases.

What is claimed is:

1. A new and distinct hybrid tea cultivar of *Rosa* plant named 'LIMking' as herein illustrated and described.

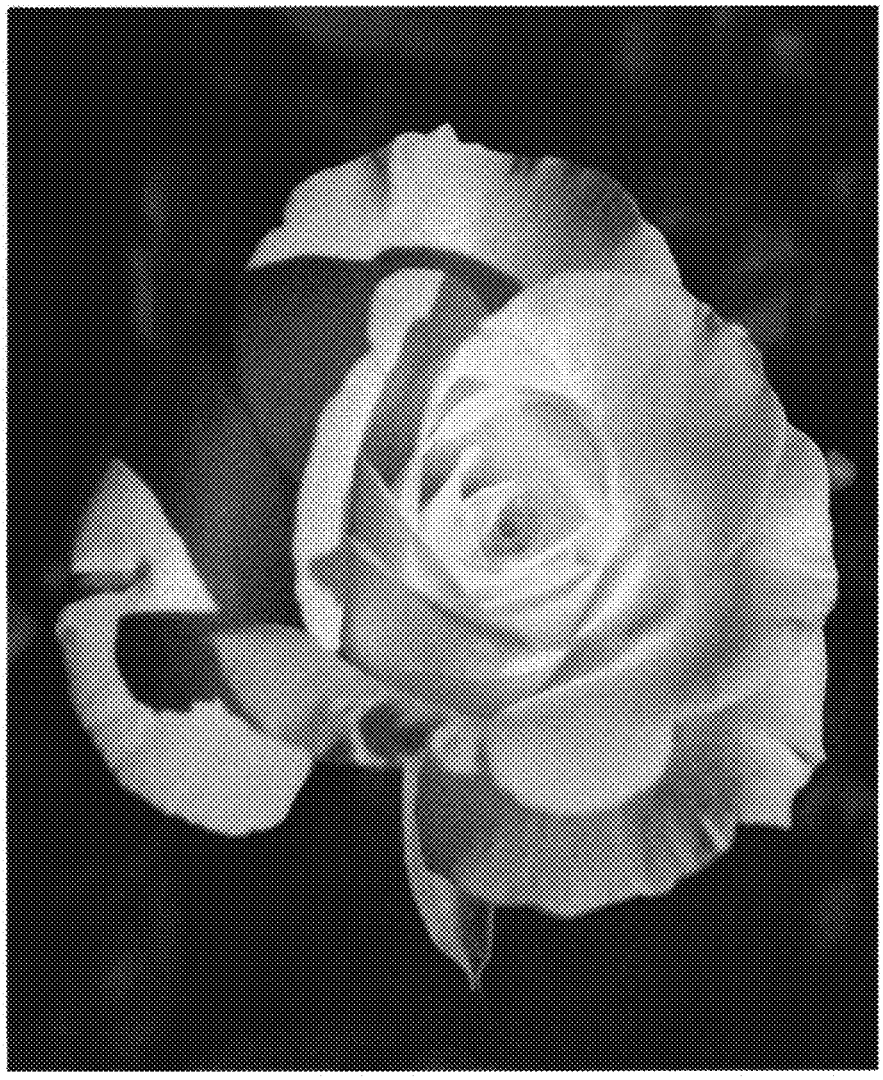

* * * * *